(12) United States Patent
Kumar

(10) Patent No.: US 12,036,270 B2
(45) Date of Patent: Jul. 16, 2024

(54) METHOD FOR IMMUNOMODULATION OF USING AZA-PODOPHYLLOTOXIN DERIVATIVES

(71) Applicant: Sistema Universitario Ana G. Mendez, San Juan, PR (US)

(72) Inventor: Ajay Kumar, San Juan, PR (US)

( * ) Notice: Subject to any disclaimer, the term of this patent is extended or adjusted under 35 U.S.C. 154(b) by 863 days.

(21) Appl. No.: 17/143,423

(22) Filed: Jan. 7, 2021

(65) Prior Publication Data

US 2021/0128705 A1 May 6, 2021

Related U.S. Application Data

(63) Continuation of application No. 14/929,641, filed on Nov. 2, 2015, now abandoned.

(60) Provisional application No. 62/121,385, filed on Feb. 26, 2015.

(51) Int. Cl.
*A61K 39/00* (2006.01)
*A61K 31/4741* (2006.01)

(52) U.S. Cl.
CPC .......... *A61K 39/00* (2013.01); *A61K 31/4741* (2013.01)

(58) Field of Classification Search
None
See application file for complete search history.

(56) References Cited

PUBLICATIONS

Kumar, Ajay, et al. "N-Hydroxyethyl-4-aza-didehydropodophyllotoxin derivatives as potential antitumor agents." European journal of pharmaceutical sciences 44.1-2 (2011): 21-26.*

* cited by examiner

*Primary Examiner* — Patrick T Lewis
(74) *Attorney, Agent, or Firm* — Eugenio J. Torres-Oyola; Victor M. Rodriguez-Reyes; Rafael Rodriguez-Muriel

(57) ABSTRACT

Disclosed is the novel use of some Aza-podophyllotoxin derivatives (AZPs) for modulation of the immune system (immunomodulation), including a method for modulating an immune response comprising administering to a subject an effective amount of at least one Aza-podophyllotoxin derivative of general formula wherein A-ring is selected from the group consisting of 1,3-dioxolane, cyclopentane, 1,4-dioxane, one methoxy, two methoxys, and ethyl; and wherein E-ring is selected from the group consisting of dimethoxyanisole, veratrol, anisole, benzene, syringol, bromobenzene, chlorobenzene, 1,2-dichlorobenzene, 2,3-dimethoxybenzene, 3,4,5-trimethoxybenzene.

18 Claims, 14 Drawing Sheets

| Average (pg/ml) | NAIVE | AP-311 | AP-312 | AP-102 | AP-103 | AP-104 | AP-205 |
|---|---|---|---|---|---|---|---|
| G-CSF | 1484.1 | 1046.8 | 1272.8 | 2207.5 | 2574.5 | 2071.2 | 7166.1 |
| GM-CSF | 9.1 | 8.8 | 8.6 | 12.8 | 8.5 | 7.7 | 8.5 |
| IL-1a | 45.9 | 13.3 | 15.5 | 17.8 | 15.4 | 19.0 | 60.9 |
| IL-1b | 24.2 | 33.7 | 35.7 | 38.0 | 36.6 | 29.3 | 63.8 |
| IL-2 | 48.5 | 23.2 | 21.2 | 52.1 | 38.9 | 38.7 | 27.5 |
| IL-3 | 113.1 | 4.2 | 10.1 | 112.7 | 20.0 | 52.8 | 57.6 |
| IL-4 | 0.2 | 1.7 | 0.0 | 0.0 | 0.8 | 0.0 | 3.5 |
| IL-5 | 0.0 | 0.0 | 0.0 | 0.0 | 0.0 | 0.0 | 0.0 |
| IL-6 | 303.9 | 551.3 | 809.7 | 772.0 | 1125.2 | 782.5 | 4351.4 |
| IL-7 | 0.0 | 0.0 | 0.0 | 0.0 | 0.0 | 0.0 | 0.0 |
| IL-9 | 44.2 | 49.4 | 35.2 | 32.8 | 56.9 | 15.1 | 48.1 |
| IL-10 | 30.0 | 21.4 | 11.6 | 25.1 | 26.0 | 41.3 | 27.4 |
| IL-12p70 | 47.1 | 73.6 | 83.7 | 87.3 | 61.8 | 66.0 | 126.4 |
| IL-13 | 0.0 | 0.0 | 0.0 | 0.0 | 0.0 | 0.0 | 0.0 |
| IL-15 | 144.2 | 167.5 | 126.0 | 146.1 | 144.3 | 109.3 | 141.1 |
| IL-17 | 302.8 | 138.9 | 148.4 | 883.1 | 153.3 | 212.9 | 249.4 |
| IL-21 | 38.6 | 38.9 | 40.5 | 35.6 | 34.5 | 24.6 | 23.1 |
| IL-23 | 0.0 | 80.0 | 0.0 | 0.0 | 0.0 | 0.0 | 239.9 |
| IFNg | 158.5 | 15.9 | 63.4 | 128.7 | 125.7 | 175.4 | 124.4 |
| TNFa | 3.1 | 0.0 | 0.0 | 0.0 | 0.0 | 313.7 | 19.0 |

Fig. 4

| SEM (pg/ml) | NAÏVE | AP-311 | AP-312 | AP-102 | AP-103 | AP-104 | AP-205 |
|---|---|---|---|---|---|---|---|
| G-CSF | 419.04 | 226.8 | 354.5 | 538.4 | 686.4 | 613.1 | 2310.8 |
| GM-CSF | 3.04 | 2.9 | 2.9 | 7.4 | 2.8 | 2.6 | 2.8 |
| IL-1a | 14.81 | 4.2 | 4.7 | 10.3 | 5.1 | 6.3 | 20.3 |
| IL-1b | 3.64 | 1.7 | 3.9 | 5.3 | 2.3 | 4.3 | 11.3 |
| IL-2 | 7.98 | 6.9 | 7.1 | 13.4 | 10.3 | 8.0 | 7.0 |
| IL-3 | 18.62 | 1.4 | 2.1 | 42.3 | 4.0 | 9.9 | 17.9 |
| IL-4 | 0.06 | 0.6 | 0.0 | 0.0 | 0.3 | 0.0 | 1.0 |
| IL-5 | 0.00 | 0.0 | 0.0 | 0.0 | 0.0 | 0.0 | 0.0 |
| IL-6 | 81.90 | 117.0 | 178.6 | 311.7 | 308.9 | 219.1 | 1409.2 |
| IL-7 | 0.00 | 0.0 | 0.0 | 0.0 | 0.0 | 0.0 | 0.0 |
| IL-9 | 14.73 | 16.5 | 11.7 | 18.9 | 19.0 | 5.0 | 13.6 |
| IL-10 | 0.70 | 3.7 | 2.5 | 4.4 | 2.6 | 7.2 | 4.4 |
| IL-12p70 | 15.69 | 16.0 | 13.9 | 28.1 | 20.6 | 11.9 | 21.7 |
| IL-13 | 0.00 | 0.0 | 0.0 | 0.0 | 0.0 | 0.0 | 0.0 |
| IL-15 | 48.06 | 55.8 | 42.0 | 84.3 | 48.1 | 36.4 | 47.0 |
| IL-17 | 100.93 | 46.3 | 49.5 | 509.8 | 51.1 | 71.0 | 83.1 |
| IL-21 | 12.85 | 13.0 | 13.5 | 20.6 | 11.5 | 8.2 | 7.7 |
| IL-23 | 0.00 | 26.7 | 0.0 | 0.0 | 0.0 | 58.5 | 80.0 |
| IFNg | 49.00 | 5.3 | 14.2 | 67.8 | 36.0 | 104.6 | 35.1 |
| TNFa | 1.03 | 0.0 | 0.0 | 0.0 | 0.0 | 0.0 | 6.3 |

Fig. 5

Library of OH-functionalized Azapodo derivatives Phase 1 & 2

| A / E | (fused bicyclic with O-CH₂-O, A+B) | (fused bicyclic, A+B) | (bicyclic with O's on A, A+B) | (MeO-phenyl, B) | (di-MeO-phenyl, B) | (Et-phenyl, B) |
|---|---|---|---|---|---|---|
| OMe, OMe, MeO (tri-OMe phenyl) | AP-101 | AP-201 | AP-301 | AP-401 | AP-501 | AP-601 |
| OMe, OMe (di-OMe phenyl) | AP-102 | AP-202 | AP-302 | AP-402 | AP-502 | AP-602 |
| OMe (mono-OMe phenyl) | AP-103 | AP-203 | AP-303 | AP-403 | AP-503 | AP-603 |

Fig. 6A

Library of OH-functionalized Azapodo derivatives Phase 1 & 2

| A \ E |  |  |  |  |  |  |
|---|---|---|---|---|---|---|
|  | AP-104 | AP-204 | AP-304 | AP-404 | AP-504 | AP-604 |
|  (OMe, OH, MeO) | AP-105 | AP-205 | AP-305 | AP-405 | AP-505 | AP-605 |
|  (OMe) | AP-106 | AP-206 | AP-306 | AP-406 | AP-506 | AP-606 |
|  (Br) | AP-107 | AP-207 | AP-307 | AP-407 | AP-507 | AP-607 |

Library of OH-functionalized Azapodo derivatives Phase 1 & 2

| E \ A |  |  |  |  |  |  |
|---|---|---|---|---|---|---|
|  (Cl) | AP-108 | AP-208 | AP-308 | AP-408 | AP-508 | AP-608 |
|  (Cl, Cl) | AP-109 | AP-209 | AP-309 | AP-409 | AP-509 | AP-609 |
|  (MeO, MeO, OMe) | AP-111 | AP-211 | AP-311 | AP-411 | AP-511 | AP-611 |
|  (MeO, MeO) | AP-112 | AP-212 | AP-312 | AP-412 | AP-512 | AP-612 |

AP102
9-(3,4-Dimethoxy-phenyl)-5-(2-hydroxy-ethyl)-6,9-dihydro-5H-1,3,7-trioxa-5-aza-dicyclopenta[b,g]naphthalen-8-one AP103
5-(2-Hydroxy-ethyl)-9-(3-methoxy-phenyl)-6,9-dihydro-5H-1,3,7-trioxa-5-aza-dicyclopenta[b,g]naphthalen-8-one AP104
5-(2-Hydroxy-ethyl)-9-phenyl-6,9-dihydro-5H-1,3,7-trioxa-5-aza-dicyclopenta[b,g]naphthalen-8-one AP205
10-(4-Hydroxy-3,5-dimethoxy-phenyl)-4-(2-hydroxy-ethyl)-3,4,6,7,8,10-hexahydro-2-oxa-4-aza-dicyclopenta[b,g]naphthalen-1-one AP311
4-(2-Hydroxy-ethyl)-11-(2,3,4-trimethoxy-phenyl)-4,7,8,11-tetrahydro-3H-2,6,9-trioxa-4-aza-cyclopenta[b]anthracen-1-one AP312
11-(2,3-Dimethoxy-phenyl)-4-(2-hydroxy-ethyl)-4,7,8,11-tetrahydro-3H-2,6,9-trioxa-4-aza-cyclopenta[b]anthracen-1-one

METHOD FOR IMMUNOMODULATION OF USING AZA-PODOPHYLLOTOXIN DERIVATIVES

BACKGROUND OF THE INVENTION

1. Field of the Invention

The present disclosure relates to the biological activity of aza-podophyllotoxin derivatives. More particularly, the use of aza-podophyllotoxin derivatives for modulation of the immune system.

2. Discussion of the Background

The innate immune response is the first line of defense against infections. The cells of the innate immune system have the capacity to recognize generic structural patterns present in pathogens called Pathogen Associated Molecular Patterns (PAMPs) and mounts an immediate immune response against these agents. This system works as a barrier that protects mammals against many ailments including infectious diseases, activate the complement system, recruits cells of the immune system to induce the process of inflammation, identifies and remove pathogens, and one of the most important features of this system, which is to activate the adaptive immune response. The term "ailment" as used in this disclosure refers to any disease, physical disorder, or complaint, generally of a chronic, acute, or mild nature. "Mosby's Medical Dictionary", 8th edition. (2009), Elsevier.

Defined broadly, immunomodulation encompasses all therapeutic interventions aimed at modifying the immune response. Runge, Marschall S., Patterson, Cam (Eds.) "Principles of Molecular Medicine", Humana Press, 2nd Ed. (2006), p. 893. More particularly, immunomodulation can include adjustment of the immune response to a desired level, as in immunopotentiation, immunosuppression, or induction of immunologic tolerance. "Miller-Keane Encyclopedia and Dictionary of Medicine, Nursing, and Allied Health", 7th Ed. (2003) by Saunders, an imprint of Elsevier, Inc.

Immunomodulation can be used as a therapeutic treatment against disease. Particularly, it can be used for the treatment of autoimmune disease. Greenwood, Steinman & Zamvil, "Statin therapy and autoimmune disease: from protein prenylation to immunomodulation", Nature Reviews Immunology 6, (May 2006) p. 358-370. The art is rich with publications relating to the use of immunomodulation, including through the use of statins (Id.); probiotics (Erickson et al., "Probiotic Immunomodulation in Health and Disease", J. Nutr. February 1, (2000) vol. 130 no. 2 403S-409S), botanical polysaccharides (Schepetkin et al., "Botanical polysaccharides: Macrophage immunomodulation and therapeutic potential", International Immunopharmacology, vol. 6, Issue 3, March 2006, Pages 317-333), fungal toxins (Bondy et al., "Immunomodulation By Fungal Toxins", Journal of Toxicology and Environmental Health, Part B: Critical Reviews Volume 3, Issue 2, 2000), and exercise (Pederson et al., "Exercise-induced immunomodulation—possible roles of neuroendocrine and metabolic factors", International Journal of Sports Medicine [1997, 18 Suppl 1:S2-7]).

Podophyllotoxin is a cyclolignan isolated from plants of genus Podophyllum pelatum L. and P. emodi L. It is an antimitotic agent known to bind tubulin and inhibits microtubule assembly causing cell cycle arrest in the metaphase and has been studied extensively as an antitumor agent. However, it causes severe gastrointestinal side effects, due to epimerization at C2 to cis-lactone. Derivatives of podophyllotoxin, namely etoposide and tenoposide have been developed and are currently used in clinic for the treatment of a variety of malignancies and CPH 82 is used to treat rheumatoid arthritis.

The structural complexity of podophyllotoxin has restricted most of the structural activity relationship (SAR) studied due to limitations in the derivatization of the parent natural compound. Selective transformation of—OMe groups present on ring E of the starting lignan would be a very difficult task.

Several new members of the podophyllotoxin derivatives have emerged as potentially superior chemotherapeutics, displaying improved water solubility and bioavailability, such as Nippon-Kayaku's NK-611 [2], GL-331 and Taiho's TOP-53 [3,4]. Podophyllotoxin derivatives also display anti-HIV-1 [5,6] and antibacterial [7] activities. Kumar et al., "Synthesis of novel functionalized 4-aza-2,3-didehydropodophyllotoxin derivatives with potential antitumor activity", J. Heterocyclic Chem., 47, 1275 (2010). There have been previous reports on the synthesis of some podophyllotoxin derivatives, particularly, functionalized 4-Aza-2,3-didehydropodophyllotoxin derivatives. Id. Also previously reported is the use of N-Hydroxyethyl-4-aza-didehydropodophyllotoxin derivatives as potential antitumor agents. Kumar et al., "N-Hydroxyethyl-4-aza-didehydropodophyllotoxin derivatives as potential antitumor agents", European Journal of Pharmaceutical Sciences 44 (2011) p. 21-26. Previous reports on the Biological Activity of N-Hydroxyethyl-4-aza-2,3-didehydropodophyllotoxin derivatives upon Colorectal Adenocarcinoma Cells have also been published. Velez et al., "Biological Activity of N-Hydroxyethyl-4-aza-2,3-didehydropodophyllotoxin Derivatives upon Colorectal Adenocarcinoma Cells", Open Journal of Medicinal Chemistry, 2014, 4, p. 1-11. However, there are no published reports on the immunomodulatory activity of N-Hydroxyethyl-4-aza-didehydropodophyllotoxin or its derivatives.

SUMMARY OF THE INVENTION

Disclosed, for the first time, is the novel use of some Aza-podophyllotoxin derivatives (AZPs) for modulation of the immune system (immunomodulation). We conducted stimulation of mouse lymphocites and measured the release of cytokines from in vitro cultures of mouse splenocytes to determine the Immunomodulatory effects of our AZPs. Cytokines are regulatory peptides that participate in host defense and repair processes and can also participate of coordination of cellular responses. Thomson et al., "The Cytokyne Handbook" 4th Ed. (2003) Elsiever Science Ltd, p. xxv. Therefore cytokines play a key role in immune response. House et al. (Eds), "Cytokines in Human Health Methods in Pharmacology and Toxicology" (2007) pp. 1-15.

Specifically, our data shows AP102, AP103, AP104, and AP205 (AZP compounds) to induce 2208, 2575, 2071, and 7166 pg/mL of GCSF, respectively, and the AP311, AP312, AP102, AP103, AP104, and AP205 induced 551, 810, 772, 1125, 782, and 4351 pg/mL of IL6, respectively. These data demonstrates the immuno-stimulatory ability of these AZP compounds.

The disclosure, both as to its configuration and its mode of operation will be best understood, and additional objects and advantages thereof will become apparent, by the following detailed description of several embodiments taken in conjunction with the accompanying drawings.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to limit the breadth of the application, which is measured by the claims, nor is it intended to be limiting as to the scope of the disclosure in any way.

BRIEF DESCRIPTION OF THE DRAWINGS

The accompanying drawings, which are incorporated herein, constitute part of the specifications and illustrate the preferred embodiments of the disclosure.

FIG. 4 Shows a chart of the average concentration of the cytokines produced by the tested AZP compounds.

FIG. 5 Shows a chart of the standard error of the mean (SEM) concentration of the cytokines produced by the tested AZP compounds.

DETAILED DESCRIPTION OF THE PREFERRED EMBODIMENTS

Figure 1:
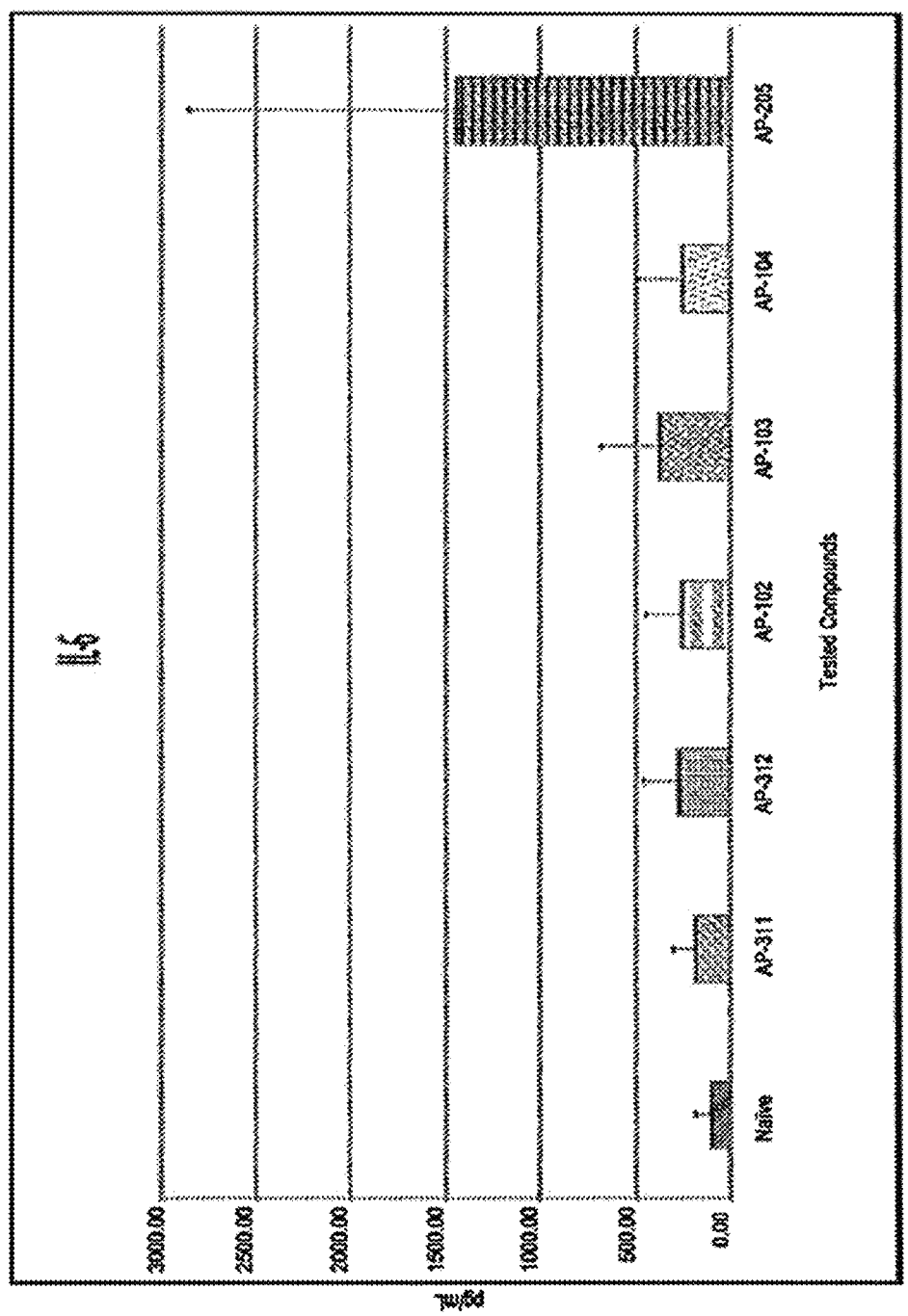
FIG. 1 Shows a graph of the concentration of IL-6 produced by the tested AZP compounds.
Figure 2:
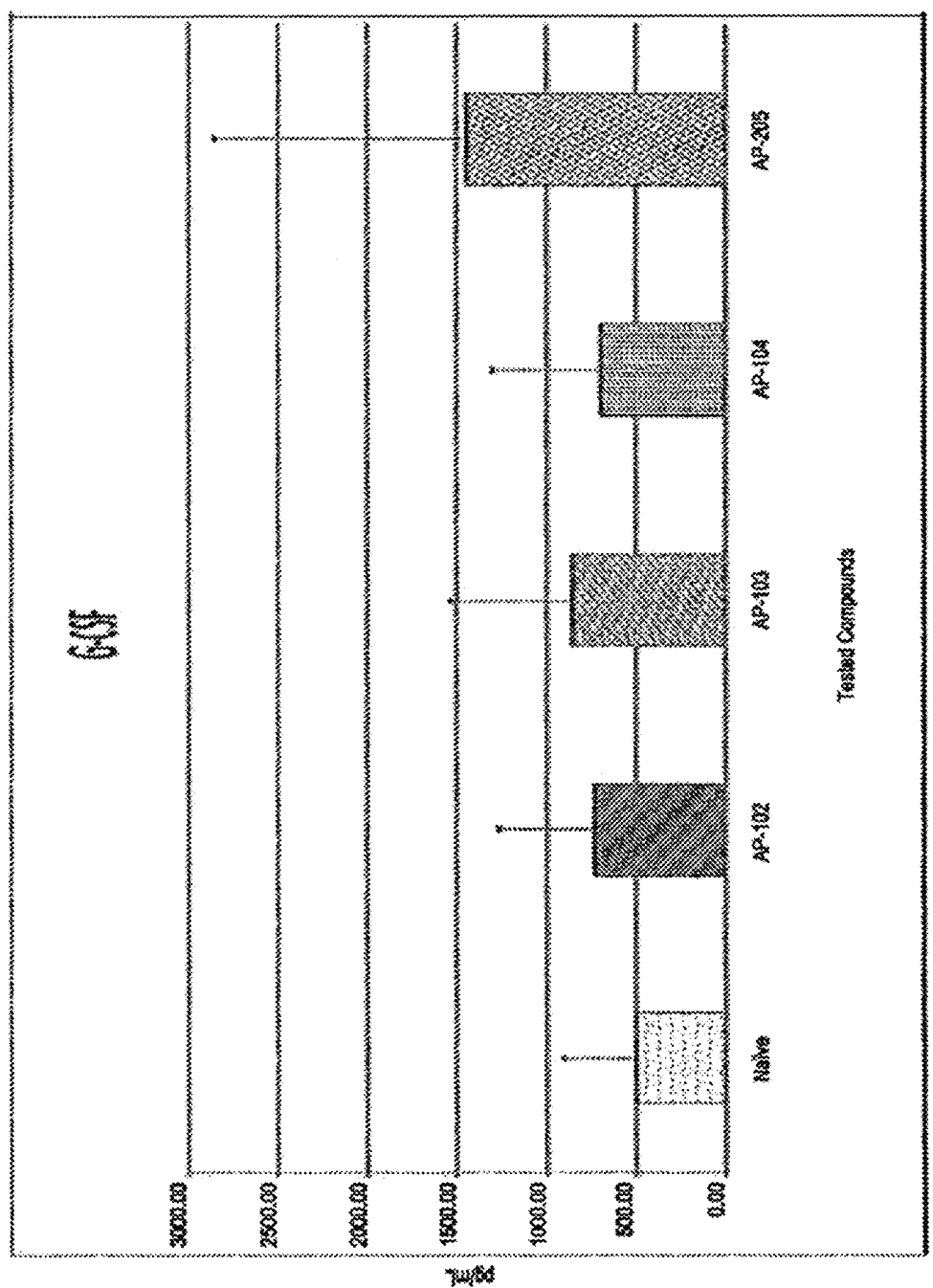
FIG. 2 Shows a graph of the concentration of G-CSF produced by the tested AZP compounds.
Figure 3:
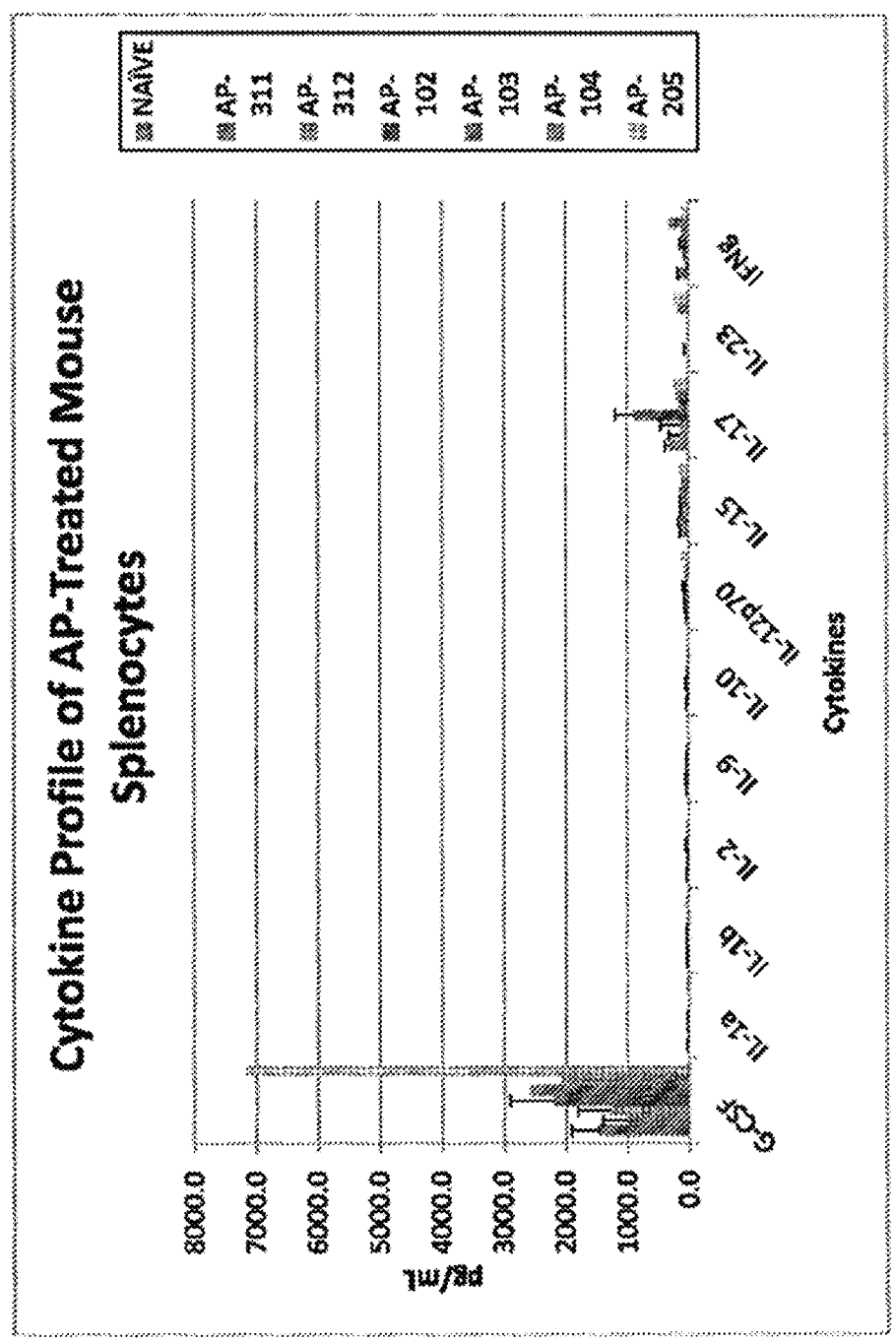
FIG. 3 Shows the profile of AP-treated mouse splenocytes. In order from left to right: naïve, AP-311, AP-312, AP-102, AP-103, AP-104, and AP-205.
Figure 6B:
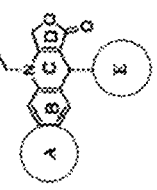
FIG. 6 shows the library of AZP compounds.
Figure 6B:
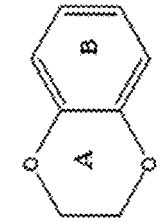
Figure 6B:
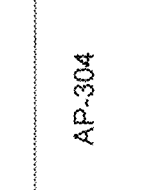
Figure 6B:
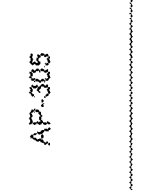
Figure 6B:
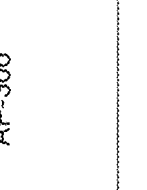
Figure 6B:
Figure 6B:
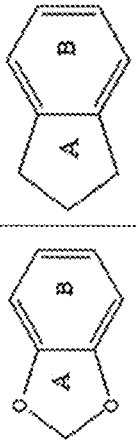
Figure 6B:
Figure 6B:
Figure 6B:
Figure 6C:
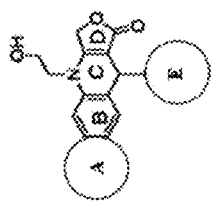
Figure 6C:
Figure 6C:
Figure 6C:
Figure 6C:
Figure 6C:
Figure 6C:
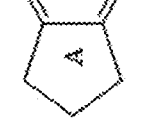
Figure 6C:
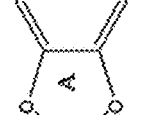
Figure 6C:
Figure 6C:
Figure 6C:
Figure 6C:
Figure 7:
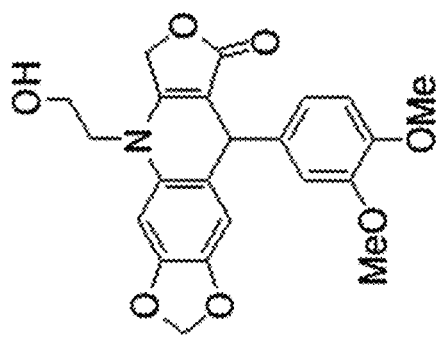
FIG. 7 shows the general structure and full name of AP102.
Figure 8:
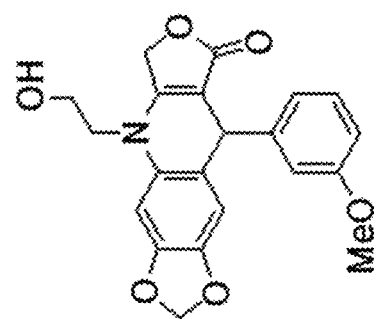
FIG. 8 shows the general structure and full name of AP103.
Figure 9:
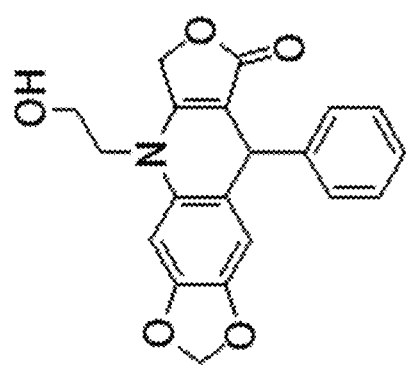
FIG. 9 shows the general structure and full name of AP104.
Figure 10:
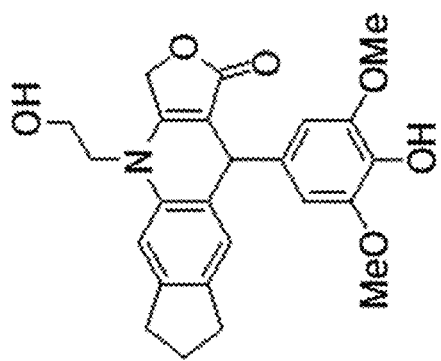
FIG. 10 shows the general structure and full name of AP205.
Figure 11:
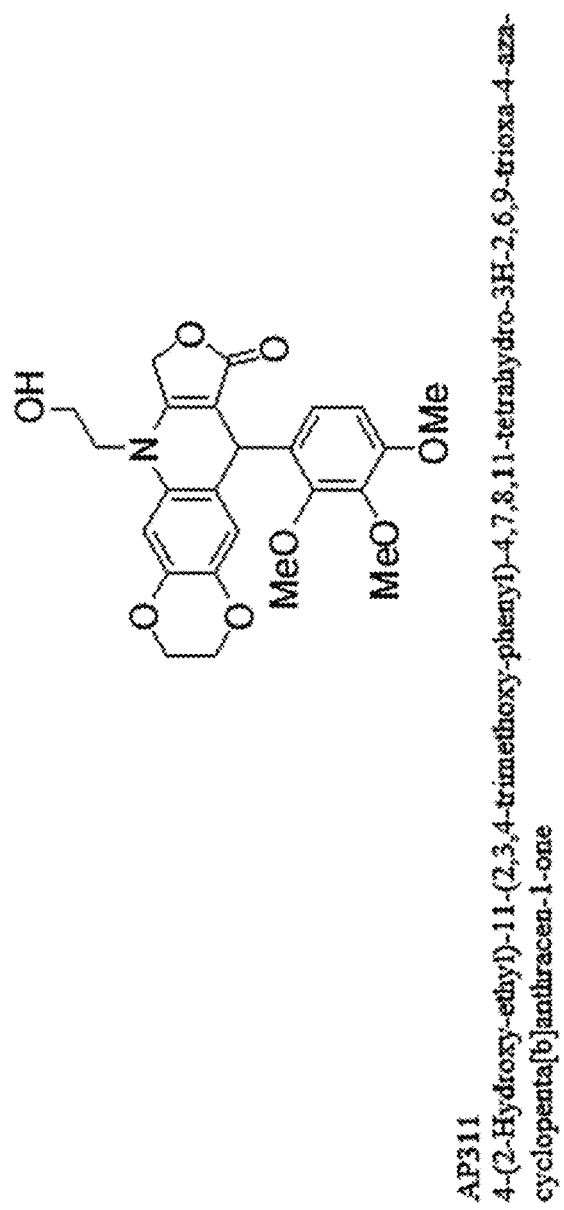
FIG. 11 shows the general structure and full name of AP311.
Figure 12:
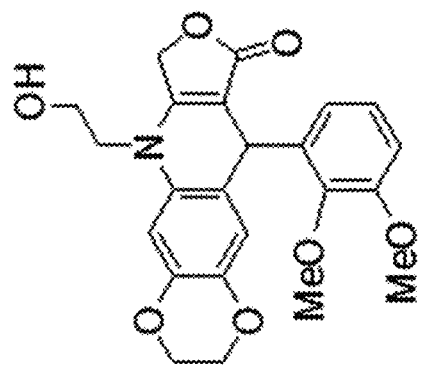
FIG. 12 shows the general structure and full name of AP312.

Disclosed below are examples of several embodiments.

A total of $2 \times 10^5$ mouse splenocytes per well were cultured in a humidified atmosphere at 37° C. and 5% CO2 in round-bottomed 96-well culture plates for five days with the AP compounds at 10 mM. Concanavalin A (10 mg/mL) and culture media were used as positive and negative controls, respectively. Plates were centrifuged at 1,200 RPM for five minutes, and supernatants were collected. The resulting cytokine profile produced after lymphocyte stimulation was analyzed using a fluorescently-labeled protein microarray chip as indicated by the manufacturer (RayBiotech, Norcross, Ga., USA).

The immunomodulatory effect of the AP compounds was assessed by in vitro stimulation of mouse lymphocytes for five days. Specifically, our preliminary data shows AP-102, AP-103, AP-104, and AP-205 to induce 2208, 2575, 2071, and 7166 pg/mL of G-CSF, respectively, and the AP-311, AP-312, AP-102, AP-103, AP-104, and AP-205 induced 551, 810, 772, 1125, 782, and 4351 pg/mL of IL-6, respectively. These data demonstrate the immunostimulatory ability of our AP compounds.

Example 1

IL-6

IL-6 is secreted by macrophages after a stimuli like PAMPs. This cytokine has an important role mediating fever and the acute phase response. The acute phase response is an early-defense system activated by the onset of infection, trauma, inflammatory processes, neoplastia, stress, and some malignant conditions. "Miller-Keane Encyclopedia and Dictionary of Medicine, Nursing, and Allied Health", Seventh Edition, (2003) by Saunders, an imprint of Elsevier, Inc.; and Cray et al., "Acute Phase Response in Animals: A Review", Comp Med. 2009 December; 59(6): pp. 517-526. It has a critical role against bacterial infections, as it is required for the resistance mechanisms against the bacteria *Streptococcus pneumonia*.

Our data shows that IL-6 is produced by all the compounds tested in this project. Specifically, 184, 270, 257, 375, 261, and 1445 pg/mL of IL-6 was produced by AP311, AP312, AP102, AP103, AP104, and AP205. respectively. Among the tested compounds, AP205 induced the highest release of IL-6.

Example 2

GCSF

GCSF is a glycoprotein produced by macrophages with the role of stimulating the production of granulocytes and stem cells from the bone marrow. It also has a role in the survival, proliferation, differentiation, and function of mature neutrophils and their precursors.

The therapeutic role of this cytokine has been commercially exploited by several pharmaceutical corporations. Specifically, cancer patients are in myelosuppression conditions, therefore, they lack of sufficient levels of white cells for disease control, making them susceptible to infections and sepsis. As GCSF has the capacity to produce granulocytes, it is used for the control of neutropenia in cancer patients, enhancing their quality of life. Moreover, during the hematopoietic stem cell transplant, GCSF is administered to the transplant donor to enhance the amount of hematopoietic stem cells before collecting by leukapheresis.

In our study, we observed levels of GCSF of 736, 858, 690, and 2336 pg/mL, when stimulated with AP102, AP103, AP104, and AP205, respectively. This information is extremely important, as GCSF is currently used for the re-establishment of neutrophils and granulocytes in cancer patients under chemotherapy. Based on this information, the compounds will perform their antitumoral activity through re-establishment of neutrophil and granulocytes.

Both, IL-6 and GCSF are important for the protection against several pathogenic infections. The capacity of IL-6 to promote neutrophil survival in the lung protects against H1N1 influenza. The interrelation between IL-6 and GCSF has been well documented. IL-6 and GCSF have a crucial role protecting against *candida* infections. Interestingly, all of our compounds produce both IL-6 and GCSF, which support their potential use against infections.

Example 3

IL-12

IL-12 is an heterodimer coded by two genes (p35 and p40). The p70 heterodimer is the active form. IL-12 is involved in the differentiation of the naive T-cells to Th1. In this sense, this cytokine has the capacity of reducing the IFN-suppression mediated by IL-4.

During the innate immune response, the macrophages are the main responsible for the production of IL-12. It stimulates the production of IFN-gamma from T and NK cells.

One of the most important roles of IL-12 is its capacity to mediate the cytotoxic activity of both, the NK and the CD8+ T-cells. IFN-gamma has an anti-angiogenic activity, blocking the formation of new blood vessels, which supports tumor growth. As IL-12 induces the release of IFN-gamma, this cytokine has an indirect antineoplastic role.

Cultured splenocytes induced 13, 29, 21, 22, and 60 pg/mL when stimulated with AP312, AP102, AP103, AP104, and AP205.

Example 4

IL-10

L-10 is mainly produced by monocytes and Th2 cells. Also, this is an anti-inflammatory cytokine, as in produced by Treg cells. This makes IL-10 as a very important regulatory cytokine.

IL-10 is a pleiotropic cytokine with several functions. It has an important role in the downregulation of the Th1-type cytokines expression. Also, it promotes the survival and proliferation of B cells, with the concomitant production of antibodies.

The IL-10 has an important role in the regulation of the immune response in the gastrointestinal tract, with an important anti-inflammatory role. The administration of IL-10 alleviates the undesired inflammatory effects of patients in conditions like Crohn disease. Also, the fact that the mastocytes also release IL-10, suggests this cytokine to have a role in allergy control.

This cytokine inhibits the production of IFN-g, IL-2, IL-3, TNF-a, and GM-CSF produced by macrophages and Treg cells. This means that it has a strong role in the regulation of the inflammatory processes. Low levels of IL-10 have been correlated with several autoimmune diseases like Multiple Sclerosis.

Culture of splenocytes induced 14 pg/mL of IL-10 when stimulated with AP104. No other compound induced the release of IL-10.

Example 5

IL-1a

IL-1a is one of the major players in the induction of inflammation, fever, and in extreme cases, sepsis. It is mainly produced by macrophages, although neutrophils, epitelial cells, and endothelial cells also produce IL-1a. It is constitutively expressed in skin keratinocytes, presumably as part of the skin protective barrier mechanism. After stimulation, a precursor of this cytokine is produced by fibroblasts, macrophages, granulocytes, eosinophils, mastocytes, and basophils. Also, IL-1a activates TNF-alpha.

Culture of splenocytes induced 20 pg/mL of IL-1a when stimulated with AP205. No other compound induced the release of IL-1a.

Example 6

IL-1b

IL-1 beta is produced as a pro-protein by activated macrophages. In its active form, it is an important mediator of inflammation with several activities that include proliferation, differentiation, and apoptosis. It could induce undesired autoimmune effects if expressed in abnormally high amounts.

Culture of splenocytes induced 12, and 19 pg/mL of IL-10 when stimulated with AP103 and AP205, respectively.

Example 7

IL-2

IL-2 has a critical role in important events like tolerance and activation of immunity. In the thyme it plays an important role during the development of Treg cells, which has important implications in the development of tolerance. During the development of the immune response, it promotes the development of the differentiation of the naive T cells to effector cells. Moreover, IL-2 promotes the differentiation of memory cells. However, one of the most important characteristics of IL-2 is its supportive role of the cell-mediated immune response, which is important against viral diseases and other intracellular pathogens.

IL-2 is licensed as part of the treatment against certain types of cancers like myelomas, renal cell cancer, lymphomas, and leukemias. In clinical studies, it has been used in a vaccine formulation as an adjuvant against viral infections.

Culture of splenocytes induced 17 pg/mL of IL-2 when stimulated with AP102. No other compound induced the release of IL-2.

Example 8

IL-9

IL-9 is produced by Th-CD4+ T-cells. It stimulates cell proliferation and prevents apoptosis. It has been found to inhibit melanomas in mouse models.

Culture of splenocytes induced 30 pg/mL of IL-9 when stimulated with AP205. No other compound induced the release of IL-9.

Example 9

IL-15

After viral infections, IL-15 is secreted, among other cells, from mononuclear phagocytes. It induces the proliferation of NK cells. Is produced as a mature protein from dendritic cells, monocytes, and macrophages. Its expression could be stimulated by GM-CSF and several PAMPs. Also, monocytic herpes virus, *Mycobacterium tuberculosis*, and *Candida albicans* infections stimulates its expression.

IL-15 regulates the activation and proliferation of T and NK cells. In the absence of the relevant antigen, it provides the signal for the survival and maintenance of memory T-cells. IL-15 and IL-2 share some receptor subunits. The balanced combination between those two cytokines is crucial for the preservation of a memory CD8+ T-cell population.

Culture of splenocytes induced 56 and 94 pg/mL of IL-15 when stimulated with AP311 and AP205, respectively.

Example 10

IL-17

IL-17 is an important mediator of the delayed-type reactions, as it increases the production of chemokines in various tissues with the intend of recruit monocytes and neutrophils to the inflammation site. This cytokine is produced by Th cells, and induced by IL-23, which result in destructive tissue damage during delayed-type reactions.

The IL-17 functions as a proinflammatory cytokine that responds to the invasion of extracellular pathogens, inducing the destruction of their extracellular matrix. It acts synergistically with TNF-alpha and IL-1.

IL-17 has various regulatory functions, in which its proinflammatory activity is the most notable. This regulatory functions are associated to the response of this cytokine to allergies. It induces the production of IL-6, GCSF, GMCSF, IL1b, TNF-a, various chemokines like IL-8, GRO-alpha, y MCP-1, and prostaglandins like PGE2 from various cell types like fibroblasts, endothelial cells, epithelial cells, keratinocytes, and macrophages. The release of these cytokines cause various effects like remodeling of the airways, which is characteristic for IL-17. The function of the IL017 is essential for the function of the Th17 cells.

Culture of splenocytes induced 294 pg/mL of IL-17 when stimulated with AP102. No other compound induced the release of IL-17.

Example 11

IL-23

Similar to IL-12, IL-23 it has a proinflammatory role. Culture of splenocytes induced 27, 58, and 80 pg/mL of IL-23 when stimulated with AP311, AP104, and AP205, respectively.

Example 12

IFN-gamma

IFn-gamma is mainly produced by NK and CD8+ T-cells. It plays a critical role in the differentiation lymphocytes from naive to effector T-cells, which also produce IFN-gamma. It has a critical role in both, the innate and the adaptive immune responses against an ample spectrum of infectious agents. Besides activate macrophages, it induces the expression of MHC II. It has antiviral, immunoregulatory, and antitumoral properties. Among its capacities are: promote the activation of the NK cells, enhances antigen-presentation by macrophages, activates iNOs, induce the production of IgG2a and IgG3 from plasma cells, promotes the differentiation of the Th1 cells, directing the response towards a cytotoxic immune response, increases the expression of MHC I in normal cells, and MHC II in APCs, promotes the adhesion of lymphocytes that migrated to the inflammation site, induces the expression of the intrinsic defense mechanisms. Also, it has a relevant role in the induction of granulomas.

IFN-gamma is licensed for the treatment of granulomatous chronic diseases and also against osteoporosis.

AP205 was the compound with the highest capacity to induce both, the highest amount and type of cytokines. It induced the release of 2336.49, 20.29, 19.45, 1444.71, 30.45, 60.14, 94.04, and 79.96 pg/mL of GCSF, IL-1a, IL-1b, IL-6, IL-9, IL-12p70, IL-15, and IL-23, respectively. From all of these cytokines, the release of GCSF is important, as in cancer patients it is used in the re-establishment of neutrophils.

AP104 was the second compound with the highest capacity of inducing cytokine release. Specifically, this compound induced the release of 690.39, 260.85, 13.78, 21.99, 58.48, and 104.58 pg/mL og GCSF, IL-6, IL-10, IL-2p70, IL-23, and IFN-gamma, respectively. No other compound induced the release of IFN-g.

AP-311 induced 183.76 and 26.66 pg/mL of IL-6 and IL-23, respectively.

AP-312 induced 11.89, 269.89, and 27.89 pg/mL of IL-1b, IL-6, and IL-12p70, respectively.

AP-102 induced 735.83, 17.36, 257.35, and 29.09 pg/mL of GCSF, IL-2, IL-6, and IL-12p70, respectively.

AP-103 induced the release of 858.15, 3.95, 535.06, and 35.70 pg/mL of GCSF, IL-1b, IL-6, and IL-12p70, respectively.

Our data shows that AP-102 expresses the cytokine milieu with the highest TH17 cytokine biased, followed by a close TH2 biased and a smaller TH1 cytokine milieu. AP-311 and AP-312, induces a strong TH2 cytokine milieu, followed by a TH17, and a smaller TH1 cytokine profile. AP-103, AP-104, and AP-205 showed high TH2-type cytokines, but equally comparably low TH1 and TH2.

It should be apparent from consideration of the above illustrative examples that numerous exceptionally valuable products and processes are provided by the present disclosure in its many aspects. Viewed in light, therefore, the specific disclosures of illustrative examples are clearly not intended to be limiting upon the scope. Numerous modifications and variations are expected to occur to those skilled in the art.

The invention claimed is:

1. An aza-podophyllotoxin derivative of general formula:

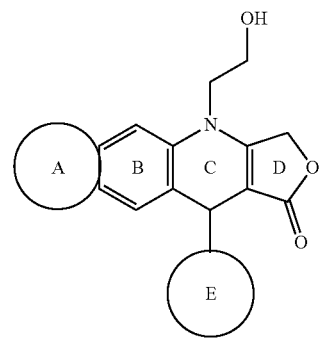

wherein a general structure A of the at least one Aza-podophyllotoxin derivative is 1,4-dioxane; and wherein a general structure E of the at least one Aza-podophyllotoxin derivative is selected from the group consisting of: 2, 3, 4-trimethoxybenzene (AP-311), and 2,3-dimethoxybenzene (AP-312).

2. The aza-podophyllotoxin derivative of general formula of claim 1, wherein E is 2, 3, 4-trimethoxybenzene (AP-311).

3. The aza-podophyllotoxin derivative of general formula of claim 1, wherein E is 2,3-dimethoxybenzene (AP-312).

4. A method for treating an ailment selected from the group consisting of fever, infection, inflammation, neoplasia, and autoimmune disease, comprising: administering to a subject an effective amount of an Aza-podophyllotoxin compound of claim 1.

5. A method for treating an ailment selected from the group consisting of fever, infection, inflammation, neoplasia, and autoimmune disease, comprising: administering to a subject an effective amount of the Aza-podophyllotoxin compound of claim 2.

6. A method for treating an ailment selected from the group consisting of fever, infection, inflammation, neoplasia, and autoimmune disease, comprising: administering to a subject an effective amount of the Aza-podophyllotoxin compound of claim 3.

7. The method of claim 4, wherein the ailment is infection.

8. The method of claim 7, wherein the infection is caused by *Streptococcus pneumoniae*.

9. A method of treating an ailment selected from the group consisting of fever, infection, inflammation, neoplasia, neutropenia, and autoimmune disease, comprising: administering to a subject an effective amount of at least one Aza-podophyllotoxin derivative selected from the group consisting of AP-102, AP-103, AP-104, and AP-205.

10. The method of claim 9, wherein the Aza-podophyllotoxin derivative is AP-102.

11. The method of claim 9, wherein the Aza-podophyllotoxin derivative is AP-103.

12. The method of claim 9, wherein the Aza-podophyllotoxin derivative is AP-104.

13. The method of claim 9, wherein the Aza-podophyllotoxin derivative is AP-205.

14. The method of claim 12, wherein the ailment is multiple sclerosis.

15. The method of claim 12, wherein the ailment is an infection caused by a virus.

16. The method of claim 10, wherein the ailment is an infection caused by a virus.

17. The method of claim 13, wherein the ailment is an infection caused by a virus.

18. The method of claim 9, wherein the ailment is an infection caused by the H1N1 influenza virus.

* * * * *